US008502012B2

(12) United States Patent
Meyer et al.

(10) Patent No.: US 8,502,012 B2
(45) Date of Patent: Aug. 6, 2013

(54) ABSORBENT STRUCTURES INCLUDING COATED ABSORBENT MATERIAL

(75) Inventors: Axel Meyer, Frankfurt (DE); Robin McKiernan, Mason, OH (US); Jean-Philippe Autran, Wyoming, OH (US); Gabriele Stiehl, Schwalbach/Ts (DE)

(73) Assignee: The Procter & Gamble Company, Cincinnati, OH (US)

(*) Notice: Subject to any disclaimer, the term of this patent is extended or adjusted under 35 U.S.C. 154(b) by 471 days.

(21) Appl. No.: 12/485,088

(22) Filed: Jun. 16, 2009

(65) Prior Publication Data

US 2010/0318049 A1 Dec. 16, 2010

(51) Int. Cl.
*A61F 13/534* (2006.01)
*B32B 5/16* (2006.01)

(52) U.S. Cl.
USPC ............................ 604/366; 428/323; 604/365

(58) Field of Classification Search
USPC ......................................... 604/366, 365, 367
See application file for complete search history.

(56) References Cited

U.S. PATENT DOCUMENTS

| | | | |
|---|---|---|---|
| 3,245,930 A | 4/1966 | McDowell et al. | |
| 3,485,777 A | 12/1969 | Gaylord | |
| 3,888,811 A * | 6/1975 | Sirota et al. | 524/310 |
| 4,959,441 A | 9/1990 | Engelhardt et al. | |
| 5,422,169 A | 6/1995 | Roe | |
| 5,837,789 A | 11/1998 | Stockhausen et al. | |
| 6,143,821 A | 11/2000 | Houben | |
| 6,310,154 B1 | 10/2001 | Babcock et al. | |
| 6,455,627 B1 | 9/2002 | De Keyzer et al. | |
| 6,458,877 B1 | 10/2002 | Ahmed et al. | |
| 6,472,478 B1 | 10/2002 | Funk et al. | |
| 6,503,979 B1 | 1/2003 | Funk et al. | |
| 6,534,572 B1 * | 3/2003 | Ahmed et al. | 524/275 |
| 6,559,239 B1 | 5/2003 | Riegel et al. | |
| 6,657,015 B1 | 12/2003 | Riegel et al. | |
| 6,710,141 B1 | 3/2004 | Heide et al. | |
| 6,911,499 B1 | 6/2005 | Brehm et al. | |
| 7,321,019 B2 | 1/2008 | Ziche | |
| 2004/0162536 A1 | 8/2004 | Becker et al. | |
| 2004/0236297 A1 | 11/2004 | Drzewiecki et al. | |
| 2005/0033256 A1 | 2/2005 | Schmidt et al. | |
| 2005/0176910 A1 | 8/2005 | Jaworek et al. | |
| 2005/0215752 A1 | 9/2005 | Popp et al. | |
| 2005/0245684 A1 | 11/2005 | Daniel et al. | |
| 2006/0155057 A1 | 7/2006 | Hermeling et al. | |
| 2006/0167215 A1 | 7/2006 | Hermeling et al. | |
| 2006/0177647 A1 | 8/2006 | Schmidt et al. | |
| 2006/0211828 A1 | 9/2006 | Daniel et al. | |
| 2006/0247377 A1 | 11/2006 | Riegel et al. | |
| 2007/0066754 A1 | 3/2007 | Loeker et al. | |
| 2008/0027402 A1 | 1/2008 | Schmidt et al. | |
| 2008/0032035 A1 | 2/2008 | Schmidt et al. | |
| 2009/0318884 A1 | 12/2009 | Meyer et al. | |
| 2010/0091431 A1 | 4/2010 | Ito | |
| 2010/0112251 A1 * | 5/2010 | Shelby et al. | 428/35.7 |

FOREIGN PATENT DOCUMENTS

| | | |
|---|---|---|
| CA | 2083417 | 11/1992 |
| DE | 40 20 780 C1 | 8/1981 |
| DE | 102 04 937 A1 | 8/2003 |
| DE | 103 55 401 A1 | 6/2005 |
| EP | 0 011 073 A1 | 5/1980 |
| EP | 083 022 A2 | 12/1982 |
| EP | 530 438 A | 4/1992 |
| EP | 547 847 A1 | 12/1992 |
| EP | 559 476 A1 | 3/1993 |
| EP | 632 068 A1 | 6/1994 |
| EP | 686 650 A1 | 6/1995 |
| EP | 937 736 A2 | 8/1999 |
| EP | 955 086 A2 | 11/1999 |
| EP | 1 199 327 A2 | 4/2002 |
| EP | 1 403 419 A1 | 3/2004 |
| EP | 1 493 453 A1 | 1/2005 |
| GB | 2119384 | 4/1983 |
| JP | 2002-526560 T | 8/2002 |
| JP | 2003-290290 A | 10/2003 |
| JP | 2007-500061 T | 1/2007 |
| JP | 2008-529590 T | 8/2008 |
| WO | WO 90/15830 A1 | 12/1990 |
| WO | WO 93/21237 A1 | 10/1993 |
| WO | WO 99/57201 A1 | 11/1999 |
| WO | WO 01/45758 A1 | 6/2001 |
| WO | WO 01/92366 A1 | 12/2001 |
| WO | WO 02/32962 A2 | 4/2002 |
| WO | WO 03/014300 A2 | 2/2003 |
| WO | WO 03/031482 A1 | 4/2003 |
| WO | WO 03/050156 A1 | 6/2003 |
| WO | WO 03/064753 A1 | 8/2003 |
| WO | WO 03/064754 A1 | 8/2003 |
| WO | WO 2006/083582 | 8/2006 |
| WO | WO 2006/083583 A2 | 8/2006 |
| WO | WO 2006/083584 | 8/2006 |
| WO | WO 2006/083585 A2 | 8/2006 |

OTHER PUBLICATIONS

Epolene Polymers as Petroleum Wax Modifiers, printed Jun. 15, 2012.*
Polymer Handbook, 3rd Edition, Ed. J. Brandrup and E. H. Immergut, VII-522,526.
Modem Superabsorbent Polymer Technology, F.L. Buchholz, A.T. Graham, Wiley 1998.
Thermoplastic Elastomers: A Comprehensive Review, eds. Legge, N.R., Holden, G., Schroeder, H.E., 1987, Chapter 2.
Ullmanns Encyclopädie der technischen Chemie, 4th Edition, vol. 19, p. 311-313.
International Search Report, dated Jun. 25, 2010, 5 pages.
All Office Actions, U.S. Appl. No. 12/477,947.

* cited by examiner

*Primary Examiner* — Susan Su
(74) *Attorney, Agent, or Firm* — Abbey A. Lopez; Charles R. Matson

(57) ABSTRACT

An absorbent layer containing water-absorbing polymeric particles that are surface-treated and that are immobilized by a matrix, formed from a thermoplastic adhesive component, including a thermoplastic polymers and a specific plasticizer, and being free of low weight average molecular weight (e.g. below 1000, or below 2000 or even below 3000 g/mole) tackifiers and plasticizers. The absorbent articles may for example be adult incontinence articles, infant (e.g. baby, toddler) diapers, including training pants, and feminine hygiene articles, such as sanitary napkins.

18 Claims, No Drawings

ABSORBENT STRUCTURES INCLUDING COATED ABSORBENT MATERIAL

FIELD OF THE INVENTION

The present disclosure relates to absorbent articles including an absorbent structure or layer containing water-absorbing polymeric particles that are surface-treated and that are immobilized by a matrix, formed from a specific thermoplastic adhesive component, including; a thermoplastic polymer and a plasticizer of a weight average molecular weight of at least 1000, and which may be free of low molecular weight (e.g. below 1000, or below 2000 or even below 3000) plasticizers; and/or including a hydrophilic, water-dispersable or water-soluble plasticizer and may optionally comprise a tackifying agent. The absorbent articles may for example be adult incontinence articles, infant (e.g. baby, toddler) diapers, including training pants, and feminine hygiene articles, such as sanitary napkins.

BACKGROUND OF THE INVENTION

An important component of disposable absorbent articles such as diapers is an absorbent core (layer) including water-absorbing polymeric material, typically hydrogel-forming water-absorbing polymeric material, also referred to as absorbent gelling material, AGM, or super-absorbent polymer, SAP. This polymeric material ensures that large amounts of bodily fluids, e.g. urine, can be absorbed by the article during its use and locked away, thus providing low rewet and good skin dryness. Especially useful water-absorbing polymeric materials are often made by initially polymerizing unsaturated carboxylic acids or derivatives thereof, such as acrylic acid, alkali metal (e.g. sodium and/or potassium) or ammonium salts of acrylic acid, alkyl acrylates, and the like. Traditionally, these water-absorbing polymers are incorporated into absorbent structures with cellulose or cellulosic fibres to provide an absorbent structure wherein the water-absorbing polymers can swell and absorb large quantities of urine with a reduced risk of gel-blocking and to ensure the right gel-bed porosity or permeability, and also to ensure the absorbent structure is stable in use or during transport. In recent years, the focus has been to make thinner absorbent structures. Hereto, it has been proposed to reduce or eliminate these cellulose fibres from the absorbent structures. However, the absorbent structure may loose part of its mechanical stability in use without the presence of cellulose fibres, and the water-absorbing structure may suffer from gel-blocking.

It has thus been proposed to use other matrix materials, in smaller quantities or volumes, such as fibrous adhesives, to provide absorbent structures that have the required permeability/porosity, and reduced gel-blocking, and that form a stable structure in use or transport. For example thermoplastic adhesives are used to form a matrix for the water-absorbing particles and to immobilise these.

In recent years there has also been ongoing development of water-absorbing polymers with improved performance, such as improved capacity and improved permeability. Various coated water-absorbing polymeric materials have been proposed to have an improved performance.

The inventors have now found that surface-modified, e.g. surface-coated, water-absorbing polymeric particles may not perform satisfactory when incorporated into an absorbent layer with certain thermoplastic adhesive matrix materials; in particular the absorbency and/or absorbency speed may be reduced, in particular in time after extended storage periods. They found that this may be due to the interaction of certain components in the adhesive thermoplastic matrix materials with the surface of the surface-modified water-absorbing polymers, rendering their surface more hydrophobic, and thereby reducing the affinity of these surfaces for hydrophilic materials like urine, and thus reducing the absorbency of urine by the water-absorbing polymers.

The inventors have now found improved absorbent articles that incorporate surface-modified water-absorbing particles, e.g. including an additional (hydrophilic) surface modification, e.g. a coating (of for example film-forming and/or elastic polymers) with a thermoplastic adhesive material that does not negatively impact the properties, e.g. hydrophilicity, and the performance of the surface-treated water-absorbing polymeric particles. These thermoplastic adhesive materials may thus be used to make (thin) absorbent layers and articles that may even be absorbent cellulosic fibre-free, but having nevertheless a good gel-bed porosity, whilst the surface-modified water-absorbing polymeric particles maintain an excellent absorbent capacity, and importantly, absorbent speed.

SUMMARY OF THE INVENTION

The present disclosure of a first embodiment herein relates to an absorbent article including an absorbent layer including surface-modified water-absorbing polymeric particles and a thermoplastic adhesive component, the layer being obtainable by:
a) obtaining a thermoplastic adhesive component, having a viscosity of from 800 to 4000 mPa·s, or for example to 3200 mPa·s, at 175° C. (as defined herein) including i) a thermoplastic polymer with a weight average molecular weight of at least 8000 g/mole; and
ii) a plasticizer of a weight average molecular weight of at least 1000 g/mole; and the thermoplastic adhesive component being substantially free of plasticizers having a weight average molecular weight below 1000 g/mole, and which may be substantially free of tackifying agents of a weight average molecular weight below 1000 g/mole;
a) obtaining surface-modified water-absorbing polymeric particles, (which may be surface coated (including partially coated), e.g. including a surface-modification that is a surface-coating of a coating agent);
b) contacting the thermoplastic adhesive component and the surface-modified water-absorbing polymeric particles, whereby the thermoplastic adhesive material forms a coating or partial coating on, and/or a fibrous matrix for, the water-absorbing polymeric particles in the layer. The adhesive component may comprise optionally a tackifying agent, as described herein.

In another embodiment, an absorbent article includes an absorbent layer including: surface-modified water-absorbing polymeric particles and a thermoplastic adhesive component, the layer being obtainable by:
a) obtaining a thermoplastic adhesive component, having a viscosity of from 800 to 4000 mPa·s, or for example to 3200 mPa·s, at 175° C. (as described herein), including:
i) a thermoplastic polymer with a weight average molecular weight of at least 8000 g/mole and optionally a tackifier, as described herein; and
ii) a plasticizer, being water-dispersible or water-soluble, having for example a water-solubility of at least 30% or at least 40% or at least 50%, as defined by the method described herein below;
b) obtaining surface-modified water-absorbing polymeric particles, (which may be surface coated, including partially coated), e.g. including a surface-modification that is a surface-coating of a coating agent;

c) contacting the thermoplastic adhesive component and the surface-modified water-absorbing polymeric particles, whereby the thermoplastic adhesive material forms a coating or partial coating on, and/or a fibrous matrix for, the surface-modified water-absorbing polymeric particles.

Hereby, the thermoplastic adhesive component may also be substantially free of plasticizers having a weight average molecular weight below 1000 g/mole, and which may be substantially free of tackifying agents of a weight average molecular weight below 1000 g/mole.

The thermoplastic adhesive component may be fibrous, for example in the form of a fibrous matrix component, and in one embodiment, it is thus a fibrous thermoplastic adhesive component.

It may have a viscosity of between 800 and 4000 mPa·s, or from 1000 mPa·s or 1200 mPa·s or from 1600 mPa·s, to 3200 mPa·s or to 3000 mPa·s or to 2800 mPa·s or to 2500 mPa·s, at 175° C., as measurable by ASTM D3236-88, using spindle 27, 20 rpm, 20 minutes preheating at the temperature, and stirring for 10 min.

Alternatively, a second thermoplastic adhesive component may be present, having for example a viscosity of between 1500 and 4500 mPa·s, or from 2000 to 4000 mPa·s, or from 2300 to 3700 mPa·s, at 149° C. and as measurable by ASTM D3236-88, using spindle 27, 50 rpm, 30 minutes stirring. Alternatively, mixtures of such adhesive materials may be used, one or more having the first viscosity parameters above, and one or more having the second viscosity parameters above The inventors found that it may be beneficial that the thermoplastic adhesive component should thus, in one embodiment herein, be free of generally hydrophobic plasticizers, and optionally free of hydrophobic tackifying agents, that can migrate (e.g. under normal storage conditions) to the surface of the surface-modified water-absorbing polymeric particles. In one embodiment, it incorporates high molecular weight plasticizer(s) that have a reduced tendency to migrate and affect the performance of the surface-modified water-absorbing polymeric particles.

In one embodiment, it incorporates a thermoplastic adhesive component that may include hydrophilic plasticizers, which have a reduced tendency to affect the performance of the surface-modified water-absorbing polymeric particles.

The surface-modified water-absorbing polymeric particles have as surface modification that is a coating or partial coating; it may be a (partial) film coating; it may be a complete coating rather than a partial coating; it may be a homogenous, uniform coating; the (partial) coating may be formed by spray-coating the water-absorbing polymeric particles with a film forming polymer, which may be an elastomeric (elastic) film-forming polymer, and which may include heat treating or annealing the thus obtained coating to form a film coating, as described herein below in detail.

In one embodiment, the thermoplastic adhesive component and the absorbent layer/core, are free of mineral oil.

In one embodiment, the thermoplastic adhesive component comprises a tackifying agent, which is hydrophilic or water-soluble or water-dispersable, as described herein, and may be free of plasticizer.

It has been found that a combination of the surface-treated, e.g. coated, water-absorbent polymers (particles) and the adhesive component described herein, and the absorbent articles with an absorbent layer with the surface-treated, e.g. coated, water-absorbent polymer particles and the adhesive component described herein, provide an improved absorbency or speed of absorbency (acquisition), e.g. after storage/aging, compared to when adhesive component outside the scope of the claims are used, and that the absorbency or speed of absorbency remains similar to surface-treated, e.g. coated, water-absorbent polymer (particles) without adhesive component, or absorbent articles with absorbent layer containing such material (after the same storage/aging).

DETAILED DESCRIPTION OF THE INVENTION

"Absorbent layer" refers to any three dimensional structure, useful to acquire and temporarily retain, or absorb and retain liquids, such as urine, menses or blood.

"Absorbent article" refers to devices that absorb and retain liquids (such as blood, menses and urine), and more specifically, refers to devices that are placed against or in proximity to the body of the wearer to absorb and contain the various exudates discharged from the body. Absorbent articles include but are not limited to diapers (including diapers with fasteners, training pants, adult incontinence diapers/pants), adult incontinence briefs, diaper holders and liners, feminine hygiene articles, including sanitary napkins and the like.

"Diaper" refers to an absorbent article generally worn by infants and incontinent persons about the lower torso; infant diaper refers to baby and toddler diapers, including training pants, worn about the lower torso.

"Disposable" is used herein to describe articles that are generally not intended to be laundered or otherwise restored or reused (i.e., they are intended to be discarded after a single use and, may be recycled, composted or otherwise disposed of in an environmentally compatible manner).

"Elastomeric" and "elastic" when used herein means that the material will exhibit stress induced deformation that is partially or completely reversed upon removal of the stress.

When used herein, the molecular weight is the weight average molecular weight and it is given in gram/mole.

Water-Absorbing Polymers and Materials

Useful for the purposes of the present disclosure are in principle all particulate water-absorbing polymers known to one skilled in the art from superabsorbent literature for example as described in Modern Superabsorbent Polymer Technology, F. L. Buchholz, A. T. Graham, Wiley 1998. The superabsorbent particles may be spherical superabsorbent particles, or vienna-sausage shaped superabsorbent particles, or ellipsoid shaped superabsorbent particles of the kind typically obtained from inverse phase suspension polymerizations; they can also be optionally agglomerated at least to some extent to form larger irregular particles. Useful for the purposes of the present disclosure are also round-shaped particles from spray—or other gas-phase dispersion polymerisations, and some commercially available irregularly shaped particles of the kind obtainable by current state of the art production processes as is more particularly described herein below by way of example.

The water-absorbing polymeric particles that are surface modified herein may be polymeric particles obtainable by polymerization of a monomer solution including i) at least one ethylenically unsaturated acid-functional monomer, ii) at least one crosslinker, iii) if appropriate one or more ethylenically and/or allylically unsaturated monomers copolymerizable with i) and iv) if appropriate one or more water-soluble polymers onto which the monomers i), ii) and if appropriate iii) can be at least partially grafted, wherein the base polymer obtained thereby is dried, classified and—if appropriate—is subsequently treated with
v) at least one post-crosslinker before being dried and thermally post-crosslinked (i.e. surface crosslinked).

(It should be understood that said surface cross-linking with a post-crosslinking agent is not considered a surface modification/coating for the purpose of the present invention).

Useful monomers i) include for example ethylenically unsaturated carboxylic acids, such as acrylic acid, methacrylic acid, maleic acid, fumaric acid, tricarboxy ethylene and itaconic acid, or derivatives thereof, such as acrylamide, methacrylamide, acrylic esters and methacrylic esters. Acrylic acid and methacrylic acid are monomers that may also be used.

The water-absorbing polymers to be used according to the present disclosure are typically crosslinked, i.e., the polymerization is carried out in the presence of compounds having two or more polymerizable groups which can be free-radically copolymerized into the polymer network. Useful crosslinkers ii) include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in the DE-A 103 31 450, mixed acrylates which, as well as acrylate groups, include further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962.

Useful crosslinkers ii) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth) acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers ii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present disclosure may utilize di(meth)acrylates of polyethylene glycols, the polyethylene glycol used having a weight average molecular weight in the range from 300 g/mole to 1000 g/mole.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixed ethoxylated or propoxylated glycerol, of altogether 3-tuply mixed ethoxylated or propoxylated trimethylolpropane, of altogether 15-tuply ethoxylated glycerol, of altogether 15-tuply ethoxylated trimethylolpropane, of altogether at least 40-tuply ethoxylated glycerol and also of altogether at least 40-tuply ethoxylated trimethylolpropane. (Where n-tuple ethoxylated means that n mols of ethylene oxide are reacted to one mole of the respective polyol with n being an integer number larger than 0.) Crosslinkers that may be used ii) are diacrylated, dimethacrylated, triacrylated or trimethacrylated multiple ethoxylated and/or propoxylated glycerols as described for example in WO 03/104301. Di- and/or triacrylates of 3- to 10-tuply ethoxylated glycerol are particularly advantageous. Di- or triacrylates of 1- to 5-tuply ethoxylated and/or propoxylated glycerol may be used. The triacrylates of 3- to 5-tuply ethoxylated and/or propoxylated glycerol may be used. These are notable for particularly low residual levels in the water-absorbing polymer (typically below 10 ppm) and the aqueous extracts of water-absorbing polymers produced therewith have an almost unchanged surface tension compared with water at the same temperature (typically not less than 0.068 N/m).

Examples of ethylenically unsaturated monomers iii) which are copolymerizable with the monomers i) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate. Useful water-soluble polymers iv) include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide, polyvinyl alcohol and starch.

Water-absorbing polymeric particles whose base polymer is lightly crosslinked may be used. The light degree of crosslinking is reflected in the high CRC value and also in the fraction of extractables.

The preparation of a suitable base polymer and also further useful hydrophilic ethylenically unsaturated monomers i) are described in DE-A 199 41 423, EP-A 686 650, WO 01/45758 and WO 03/14300.

The reaction may be carried out in a kneader as described for example in WO 01/38402, or on a belt reactor as described for example in EP-A-955 086.

The acid groups of the base polymers obtained may be 0-100 mol %, 25-100 mol %, 65-90 mol % and 68-80 mol % neutralized, for which the customary neutralizing agents can be used, for example ammonia, or amines, such as ethanolamine, diethanolamine, triethanolamine or dimethylaminoethanolamine, alkali metal hydroxides, alkali metal oxides, alkali metal carbonates or alkali metal bicarbonates and also mixtures thereof, in which case sodium and potassium may be alkali metal salts, and may be sodium hydroxide, sodium carbonate or sodium bicarbonate and also mixtures thereof. Typically, neutralization is achieved by admixing the neutralizing agent as an aqueous solution or as an aqueous dispersion or else as a molten or as a solid material.

The water-absorbing polymers to be used can be post-crosslinked in one version of the present disclosure, prior to applying the coating agent herein. Useful post-crosslinkers include compounds including two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. Useful post-crosslinkers v) are further the to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by DE-A 103 34 584 bicyclic amide acetals, by EP-A 1 199 327 oxetanes and cyclic ureas and by WO 03/031482 morpholine-2,3-dione and its derivatives.

Post-crosslinking is typically carried out by spraying a solution of the post-crosslinker onto the base polymer or the dry base-polymeric particles. Spraying is followed by thermal drying, and the post-crosslinking reaction can take place not only before but also during or after drying.

The water-absorbing polymeric particles can have a particle size distribution in the range from 45 μm to 4000 μm. Particle sizes used in the hygiene sector may range from 45 μm to 1000 μm, from 45-850 μm, and from 100 μm to 850 μm. Water-absorbing polymeric particles having a narrow particle size distribution may be coated, for example 100-850 μm, or even 100-600 μm.

Narrow particle size distributions herein may be those in which not less than 80% by weight of the particles, not less than 90% by weight of the particles and not less than 95% by weight of the particles are within the selected range; this fraction can be determined using the familiar sieve method of EDANA 420.2-02 "Particle Size Distribution". Selectively, optical methods can be used as well, provided these are calibrated against the accepted sieve method of EDANA.

Narrow particle size distributions may have a span of not more than 700 μm, of not more than 600 μm, and of less than 400 μm. Span here refers to the difference between the coarse sieve and the fine sieve which bound the distribution. The coarse sieve is not coarser than 850 μm and the fine sieve is not finer than 45 μm.

Surface Modification

The water-absorbing polymeric particles herein include a surface modification, e.g. of a surface modifying agent. It should be understood that for the purpose of the present disclosure this does not include any of the (post) surface-crosslinking agents that may modify the surface, described above. Thus, the water-absorbing polymeric particles herein may comprise (post) surface-crosslinking agents and they may thus be surface crosslinked, in addition to comprising a surface modification and a surface modifying agent, e.g. a (partial) coating and coating agent as described herein. In one embodiment, the water-absorbing polymeric particles do not comprise a (post) surface -crosslinking.

In one embodiment, the surface-modification is a surface coating or partial surface coating of a coating agent, and the surface-modification is thus a surface coating.

The coating agent may be such that it can render the water-absorbing polymeric particles, coated or partially coated with the agent, more hydrophilic (compared to the uncoated water-absorbing polymeric particles), as described below. In another embodiment, the coating agent is such that it provides a coating or partial coating on the water-absorbing polymeric particles, which may be hydrophilic, as described herein below.

In a first embodiment, the water-absorbing polymeric particles may be coated or partially coated with a polymer. In one embodiment, the water-absorbing polymeric particles may be coated or partially coated with an elastic polymer or a film-forming polymer or may be with an elastic film-forming polymer, which forms an elastomeric (elastic) film coating on the particle.

The term "polymer" as used herein refers to single polymers and blends of polymers. Film-forming means that the respective polymer can readily be made into a film, i.e. layer or coating, upon evaporation of the solvent in which it is dissolved or dispersed. The polymer may for example be thermoplastic or crosslinked.

In one embodiment, the polymeric material of the coating is a phase separating elastic polymeric material. 'Phase-separating' elastic polymeric material, when used herein, means that a film of the elastic material (i.e. prior to use in the coating agent and application to the water-swellable polymers) has at least two distinct spatial phases which are distinct and separated from one another, due to their thermodynamic incompatibility. The incompatible phases are comprised of aggregates of only one type of repeat unit or segment of the elastic material. This can for example occur when the elastic material is a block (or segmented) copolymer, or a blend of two immiscible polymers. The phenomenon of phase separation is for example described in: Thermoplastic Elastomers: A Comprehensive Review, eds. Legge, N. R., Holden, G., Schroeder, H. E., 1987, Chapter 2.

Typically, the phase separation occurs in a block copolymer, whereby the segment or block of the copolymer that has a Tg below room temperature (i.e. below 25° C.) is said to be the soft segment or soft block and the segment or block of the copolymer that has a Tg above room temperature is said to be the hard segment or hard block. Such polymeric material may thus be a coating agent for herein. The Tg's, as referred to herein, may be measured by Differential Scanning Calorimetry (DSC) to measure the change in specific heat that a material undergoes upon heating. The DSC measures the energy required to maintain the temperature of a sample to be the same as the temperature of the inert reference material (eg. Indium). A Tg is determined from the midpoint of the endothermic change in the slope of the baseline. The Tg values are reported from the second heating cycle so that any residual solvent in the sample is removed.

In addition, the phase separation can also be visualized by electron microscopy particularly if one phase can be stained preferentially. Also atomic force microscopy has been described as a particularly useful technique to characterize the morphology (phase-separating behavior) of the thermoplastic polyurethanes, described herein after.

The coating may be a homogeneous and/or uniform coating on the surface of the water-absorbing polymeric particles; the coating agent may be applied at a level of from 0.1% to 5%, or may be from 0.2% to 1%, by weight of the surface-modified water-absorbing polymeric particles.

Suitable polymers, usable as coating or partial coating, include polyamines and polyesters. The polyamine may have a molecular weight of at least 10,000, and may be at least 50,000.

Examples of polyamines include polyvinylamines, polyallylamines, polyalkyleneamines, and polyethylene imines, and mixtures thereof.

Polymers that may be used for coating are film forming and have elastic/elastomeric properties. Polymers having film-forming and also elastic properties are generally suitable, such as copolyesters, copolyamides, polyolefins, styrenic block copolymers, including styrene-isoprene block copolymers, styrene-butadiene block copolymers, and polyurethanes, and blends thereof, optionally blends including at least polyurethanes. Some include polyurethanes and polyurethane blends.

The surface coating may include or be made of polymers that have two or more glass transition temperatures (Tg) (determined by ASTM E1356-03). Ideally, the polymers used exhibit the phenomenon of phase separation, i.e., they contain two or more different blocks of low and high Tg side by side in the polymer (Thermoplastic Elastomers: A Comprehensive Review, eds. Legge, N. R., Holden, G., Schroeder, H. E., 1987, chapter 2). Some may be phase-separating polymers, and especially polyurethanes, herein include one or more phase-separating block copolymers, having a weight average molecular weight Mw of at least 5 kg/mol, and may be at least 10 kg/mol and higher.

In one embodiment such a block copolymer has at least a first polymerized homopolymer segment (block) and a second polymerized homopolymer segment (block), polymerized with one another, whereby the first (soft) segment may have a Tg1 of less than 25° C. or even less than 20° C., or even less than 0° C., and the second (hard) segment has a Tg2 of at least 50° C., or of 55° C. or more, and may be 60° C. or more or even 70° C. or more.

In another embodiment, such a block copolymer has at least a first polymerized polymer segment (block) and a second polymerized polymer segment (block), polymerized with one another, whereby the first (soft) segment may have a Tg1 of less than 25° C. or even less than 20° C., or even less than 0° C., and the second (hard) segment has a Tg2 of at least 50° C., or of 55° C. or more, may be 60° C. or more or even 70° C. or more.

The weight average molecular weight of a first (soft) segment (with a Tg of less than 25° C.) may be at least 500 g/mol, at least 1000 g/mol or even at least 2000 g/mol, and maybe less than 8000 g/mol, and may be less than 5000 g/mol.

However, the total of the first (soft) segments may be 20% to 95% by weight of the total block copolymer, or even from 20% to 85% or may be from 30% to 75% or even from 40% to 70% by weight. Furthermore, when the total weight level of soft segments is more than 70%, it may be that an individual soft segment has a weight average molecular weight of less than 5000 g/mol.

The film-forming polymer is typically such that at least some of the resulting coating on the water-swellable polymers herein is not water-soluble and, may be not water-dispersible once a film has been formed.

Polyurethanes may be film-forming polymers. They can be applied to the water-absorbing polymeric particles as a solution or as a dispersion. Some may be aqueous dispersions, further described below.

For fast wetting, the coating agent (film-forming, elastic) polymer may be hydrophilic.

The film-forming polymer can for example be applied from a solution or an aqueous solution or in another embodiment can be applied from a dispersion or from an aqueous dispersion. The solution can be prepared using any suitable organic solvent for example acetone, isopropanol, tetrahydrofuran, methyl ethyl ketone, dimethyl sulfoxide, dimethylformamide, N-methylpyrrolidone, chloroform, ethanol, methanol or mixtures thereof.

Polymers can also be blended prior to coating by blending their respective solutions or their respective dispersions. Alternatively polymers can be blended by simultaneous spraying or subsequent spraying. In particular, polymers that do not fulfil the elastic criteria by themselves can be blended with polymers that do fulfil these criteria and yield a blend that is suitable for coating.

Suitable elastic polymers which are applicable from solution are for example Vector® 4211 (Dexco Polymers, Texas, USA), Vector 4111, Septon 2063 (Septon Company of America, A Kuraray Group Company), Septon 2007, Estane® 58245 (Noveon, Cleveland, USA), Estane 4988, Estane 4986, Estane® X-1007, Estane T5410, Irogran PS370-201 (Huntsman Polyurethanes), Irogran VP 654/5, Pellethane 2103-70A (Dow Chemical Company), Elastollan® LP 9109 (Elastogran).

In one embodiment the polymer is in the form of an aqueous dispersion and in another embodiment the polymer is an aqueous dispersion of a polyurethane.

The synthesis of polyurethanes and the preparation of polyurethane dispersions are well described for example in Ullmann's Encyclopedia of Industrial Chemistry, Sixth Edition, 2000 Electronic Release.

The polyurethane may be hydrophilic and in particular surface hydrophilic. This hydrophilicity may also be achieved (enhanced) via addition of fillers, surfactants, deagglomeration and coalescing agents. The surface hydrophilicity may be determined by methods known to those skilled in the art. In one execution, the hydrophilic polyurethanes are materials that are wetted by the liquid that is to be absorbed (0.9% saline; urine). They may be characterized by a contact angle that is less than 90 degrees. Contact angles can for example be measured with ASTM D 5725-99.

In one embodiment, the hydrophilic properties are achieved as a result of the polyurethane including hydrophilic polymer blocks, for example polyether groups having a fraction of groups derived from ethylene glycol (CH2CH2O) or from 1,4-butanediol (CH2CH2CH2CH2O) or from 1,3-propanediol (CH2CH2CH2O) or from 1,2-propanediol (—CH(CH3)-CH2O—), or mixtures thereof.

It is further possible to obtain hydrophilic properties for the polyurethanes through an elevated fraction of ionic groups, and may be carboxylate, sulfonate, phosphonate or ammonium groups. The ammonium groups may be protonated or alkylated tertiary or quarternary groups. Carboxylates, sulfonates, and phosphates may be present as alkali-metal or ammonium salts. Suitable ionic groups and their respective precursors are for example described in "Ullmanns Encyclopädie der technischen Chemie", 4th Edition, Volume 19, p. 311-313 and are furthermore described in DE-A 1 495 745 and WO 03/050156.

The hydrophilicity of some polyurethanes facilitates the penetration and dissolution of water into the water-absorbing polymeric particles, which are enveloped by the film-forming polymer. The coatings with these polyurethanes are notable for the fact that the mechanical properties are not excessively impaired even in the moist state, despite the hydrophilicity.

It is well understood by those skilled in the art that "polyurethanes" is a generic term used to describe polymers that are obtained by reacting di- or polyisocyanates with at least one di- or polyfunctional "active hydrogen-containing" compound. "Active hydrogen containing" means that the di- or polyfunctional compound has at least 2 functional groups which are reactive toward isocyanate groups (also referred to as reactive groups), e.g. hydroxyl groups, primary and secondary amino groups and mercapto (SH) groups.

It also is well understood by those skilled in the art that polyurethanes also include allophanate, biuret, carbodiimide, oxazolidinyl, isocyanurate, uretdione, and other linkages in addition to urethane and urea linkages.

In one embodiment the block copolymers useful herein may be polyether urethanes and polyester urethanes. Some may be polyether urethanes including polyalkylene glycol units, especially polyethylene glycol units or poly(tetramethylene glycol) units. In one embodiment polyester urethanes are used as they often exhibit better mechanical properties in the wet state when compared to polyether urethanes.

The polyurethanes used according to the present disclosure are generally obtained by reaction of polyisocyanates with active hydrogen-containing compounds having two or more reactive groups. These include
  a) high molecular weight compounds having a weight average molecular weight in the range which may be 300 to 100 000 g/mol and may be from 500 to 30 000 g/mol
  b) low molecular weight compounds and c) compounds having polyether groups, especially polyethylene oxide groups or poly(tetramethylene glycol) groups and a weight average molecular weight in the range from 200 to 20 000 g/mol, the polyether groups in turn having no reactive groups.

Polyisocyanates may have an average of about two or more isocyanate groups, and may have an average of about two to about four isocyanate groups and include aliphatic, cycloaliphatic, araliphatic, and aromatic polyisocyanates, used alone or in mixtures of two or more. Diisocyanates may be used. Aliphatic and cycloaliphatic polyisocyanates, diisocyanates may be used.

Specific examples of suitable aliphatic diisocyanates include alpha, omega-alkylene diisocyanates having from 5 to 20 carbon atoms, such as 1,6-hexamethylene diisocyanate, 1,12-dodecane diisocyanate, 2,2,4-trimethylhexamethylene diisocyanate, 2,4,4-trimethyl-hexamethylene diisocyanate, 2-methyl-1,5-pentamethylene diisocyanate, and the like. Polyisocyanates having fewer than 5 carbon atoms can be used. Some aliphatic polyisocyanates include 1,6-hexamethylene diisocyanate, 2,2,4-trimethyl-hexamethylene diisocyanate.

Examples of suitable aromatic diisocyanates include 4,4'-diphenylmethane diisocyanate, toluene diisocyanate, their isomers, naphthalene diisocyanate, and the like. Aromatic diisocyanate may be toluene diisocyanate.

Examples of high molecular weight compounds a) having 2 or more reactive groups are such as polyester polyols and polyether polyols, as well as polyhydroxy polyester amides, hydroxyl-containing polycaprolactones, hydroxyl-containing acrylic copolymers, hydroxyl-containing epoxides, polyhydroxy polycarbonates, polyhydroxy polyacetals, polyhydroxy polythioethers, polysiloxane polyols, ethoxylated polysiloxane polyols, polybutadiene polyols and hydrogenated polybutadiene polyols, polyacrylate polyols, halogenated polyesters and polyethers, and the like, and mixtures thereof. The polyester polyols, polyether polyols, polycarbonate polyols, polysiloxane polyols, and ethoxylated polysiloxane polyols may be used. In some embodiments, polyesterpolyols, polycarbonate polyols, polyalkylene ether polyols, and polytetrahydrofurane are used. The number of functional groups in the aforementioned high molecular weight compounds may be on average in the range from 1.8 to 3 and may be in the range from 2 to 2.2 functional groups per molecule.

The polyester polyol may be a diol. Polyester diols may include poly(butanediol adipate); hexanediol adipic acid and isophthalic acid polyesters such as hexaneadipate isophthalate polyester; hexanediol neopentyl glycol adipic acid polyester diols, e.g., Piothane 67-3000 HNA (Panolam Industries) and Piothane 67-1000 HNA, as well as propylene glycol maleic anhydride adipic acid polyester diols, e.g., Piothane SO-1000 PMA, and hexane diol neopentyl glycol fumaric acid polyester diols, e.g., Piothane 67-SO0 HNF. Other polyester diols may include Rucoflex® S101.5-3.5, S1040-3.5, and S-1040-110 (Bayer Corporation).

Polyethers may include poly(ethylene glycol), poly(propylene glycol), polytetrahydrofuran, and co[poly(ethylene glycol)-poly(propylene glycol)], or blends thereof. In case that propylene oxide and ethylene oxide are copolymerized, these polypropylene-co-polyethylene polymers can be used as random polymers or block copolymers.

Polycarbonates include those obtained from the reaction of diols such 1,3-propanediol, 1,4-butanediol, 1,6-hexanediol, diethylene glycol, triethylene glycol, tetraethylene glycol, and the like, and mixtures thereof with dialkyl carbonates such as diethyl carbonate, diaryl carbonates such as diphenyl carbonate or phosgene.

Some aqueous polyurethane dispersions are Hauthane HD-4638 (ex Hauthaway), Hydrolar® HC 269 (COIMolm, Italy), Impraperm® 48180 (Bayer Material Science AG, Germany), Lurapret® DPS (BASF Aktiengesellschaft, Germany), Astacin® Finish LD 1603 (BASF Aktiengesellschaft, Germany), Permax® 120, Permax 200, and Permax 220 (Noveon, Brecksville, Ohio), Syntegra YM2000 and Syntegra YM2100 (Dow, Midland, Mich.), Witcobond® G-213, Witcobond G-506, Witcobond G-507, Witcobond 736 (Uniroyal Chemical, Middlebury, Conn.), Astacin Finish PUMN TF, Astacin TOP 140, Astacin Finish SUSI (all BASF) and Impranil® DLF (anionic aliphatic polyester-polyurethane dispersion from Bayer Material Science).

More particularly, the polyurethanes described can be used in mixtures with each other or with other film-forming polymers, fillers, oils, blowing aids, water-soluble polymers or plasticizing agents in order that particularly advantageous properties may be achieved with regard to hydrophilicity, water perviousness and mechanical properties.

In one embodiment in a first step one film forming polymer dispersion or solution, which may be a polyurethane dispersion, is applied onto the surface of the water absorbing particles followed by at least one second step applying a different film forming polymer dispersion onto the surface of the already coated water absorbing particles. In some embodiments, this second film-forming polymer may not be a polyurethane but forms a film, which may be less tacky than the polyurethane. In one embodiment this second film is more hydrophilic than the polyurethane. A process may be, wherein the second, non polyurethane dispersion, which forms more hydrophilic films than polyurethanes is sprayed separately either immediately after coating the polyurethane dispersion before subsequent heat treatment according to step b) or finally after the heat treatment. In one embodiment this second film is more hydrophilic than the polyurethane.

The second coating agent, e.g. dispersion, may also be mixed with the first coating agent, to form one mixture, e.g. dispersion, which is then applied to the water-absorbing polymeric particles.

The elastic and/or film-forming polymer can be applied as a solid material, as a hotmelt, and may be as a dispersion, including an aqueous dispersion, and/or as an aqueous solution or as an organic solution, to the particles of the water-absorbing addition polymer. The form in which the elastic and/or film-forming polymer, especially the polyurethane is applied to the water-absorbing polymeric particles may be an organic solution or may be as an aqueous dispersion.

Useful solvents include solvents, which make it possible to establish not less than 30% or not less than 40% by weight concentrations of the elastic and/or film-forming polymer, e.g. polyurethane, in the respective solvent or mixture. As examples there may be mentioned alcohols, esters, ethers, ketones, amides, and halogenated hydrocarbons; examples include methyl ethyl ketone, acetone, isopropanol, tetrahydrofuran, dimethylformamide, N-methylpyrrolidone, chloroform and mixtures thereof. Solvents which are polar, aprotic and boil below 100° C. are particularly advantageous.

The coating may be applied in a fluidized bed reactor. The water-absorbing particles are introduced as generally customary, depending on the type of the reactor, and are generally coated by spraying with the elastic and/or film-forming polymer as a solid material or may be as a polymeric solution or dispersion. Aqueous dispersions of the film-forming polymer may be used for this.

The concentration of polymer in the solution or dispersion may be in the range from 1% to 60% by weight, may be in the range from 5% to 40% by weight and may be in the range from 10% to 30% by weight.

In one embodiment herein the surface-modified water-absorbing material herein may be obtainable by a process including the steps of:
 a) spray-coating water-absorbing polymeric particles with an elastic and/or film-forming polymer in a fluidized bed reactor in the range from 0° C. to 150° C. and
 b) heat-treatment of the coated particles at a temperature above 50° C.

In another embodiment herein, the surface-modification is a surface coating of a coating agent that renders the water-absorbing polymeric particles more hydrophilic, i.e. such that the resulting coated particulate super absorbent material has a contact angle of equal or less than 90° and a corresponding cos CAm (as defined in co-pending application EP1493453A), the cos CAm being more than 0.3.

The coating agent is typically such that the contact angle of the coated water-absorbent polymeric particles is changed versus the contact angle of the uncoated water-absorbing polymeric particles, i.e. such that the uncoated water-absorbing polymeric particles before being coated with the coating agent, have a certain contact angle CAp and a cos CAp (as defined in co-pending application EP1493453A) and the coated water-absorbing polymeric particles have a certain contact angle CAm and a cos CAm (as defined in the co-pending application), and the ratio cos CAm/cos CAp is at least 1.5.

Some organic monomer or dimer compounds useful as such a surface-modifying agent, i.e coating agent, have at least one polar group. Some organic monomer and dimer coating agents may have a weight average molecular weight of less than 1000 g/mole, or even less than 750 g/mol or even less than 500 g/mole. Some organic monomer or dimer coating agents herein are water miscible organic compound that provide a surface tension reduction of 15% or less, or even 10% or less, or even less than 5% or even about 0%, as can be determined with the test set out in EP1493453.

Monomer or dimer organic coating agent may have 2 to 9 carbon atoms in a single linear or branched chain, and in addition at least one polar group including at least one oxygen atom bound to a hydrogen atom. (If the polar group contains one or more carbon atom, then this is not included in the 2-9 carbon atoms in the compound.).

Some are polar groups having an O—H group. The organic compound or component of the coating agent may be an organic derivates of an oxo acid, or salt or ester thereof. Typical are derivatives of oxo acids of carbon, sulfur, phosphor; thus, the organic compounds or components of the coating agent herein are for example derivatives of a carboxylic acid, phosphoric acid and/or sulphoric acid.

The monomer or dimer coating agent may include a compound that may have at least two polar groups, at least one cationic group (which may be an amine group, guanidine group), and may have at least one cationic and at least one anionic polar group.

Thermoplastic Adhesive Component

The absorbent layer may include a thermoplastic adhesive component. It may be beneficial, e.g. for process reasons and/or performance reasons, that the thermoplastic adhesive component has a viscosity of between 800 and 4000 mPa·s, or from 1000 mPa·s or 1200 mPa·s or from 1600 mPa·s to 3200 mPa·s or to 3000 mPa·s or to 2800 mPa·s or to 2500 mPa·s, at 175° C., as measurable by ASTM D3236-88, using spindle 27, 20 pmp, 20 minutes preheating at the temperature, and stirring for 10 min.

The thermoplastic adhesive component may have a softening point of a temperature between 60° C. and 150° C., between 75° C. and 135° C., or between 90° C. and 130° C., or between 100° C. and 115° C., as can be determined with ASTM E28-99 (Herzog method; using glycerine).

The thermoplastic adhesive component may be present at a level of for example 0.5% to 50% by weight of the absorbent layer, or from 1.0% or from 1.5% or from 3% or from 5% or from 7% to 35% or to 30% or to 20% or to 15% by weight of the absorbent layer.

The thermoplastic adhesive component may be present in the absorbent layer such that the weight ratio of the water-absorbing polymeric particles to the thermoplastic adhesive component is from 1:1 to 50:1, or from 2:1 to 40:1 or to 35:1, or from 3:1 to 25:1 or to 20:1, or from 3:1 to 15:1

The thermoplastic adhesive component includes thermoplastic polymers. The polymers have typically a weight average molecular weight of at least 8000, or at least 12,000, or at least 15,000 (g/mole). The thermoplastic material may include a single thermoplastic polymer or a blend of thermoplastic polymers.

The thermoplastic polymer may have a glass transition temperature (Tg) below room temperature (20° C.), as can be measured by ASTM E1356-03. It may have two or more Tg's, and then may have at least one Tg, but typically not all Tg's, are below room temperature. A wide variety of thermoplastic polymers are suitable for use in the present disclosure.

Some are thermoplastic polymers, co-polymers or block co-polymers with a polyolefin, polyether, polyester and/or polyamide units.

Exemplary (typically hydrophilic) thermoplastic polymers include: polyurethanes, polyether esters, polyether amides (e.g. Pebax).

Example polymers include ethylene vinyl acetate polymers (EVA), or amorphous poly-alpha olefin (APAO). Further exemplary polymers are (styrenic) block copolymers (SBC), including A-B-A triblock structures, A-B diblock structures and (A-B)n radial block copolymer structures wherein the A blocks are non-elastic polymer blocks, typically including polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. The thermoplastic polymer may include a styrene-isoprene-styrene (SIS), and/or a styrene-butadiene-styrene (SBS) and/or styrene-ethylene/butylene-styrene (SEBS), or may be SIS. The triblock may for example consist of about 14-22 weight % styrene for SIS copolymers and above 25 weight % styrene for SBS copolymers. Triblock can also contain 0-50 weight % of diblock.

One example thermoplastic polymer is an EVA polymer, i.e. copolymers of ethylene and vinyl acetate. The vinyl acetate is generally in the range of 15-40 weight %.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alphaolefins, for example of propene-ethylene, propene-butene, propene-hexene, or terpolymers of propene-butene-ethene made by a Ziegler-Natta polymerization.

In one embodiment, the thermoplastic adhesive component includes a plasticizer that has have a weight average Mw (in gram/mole) of at least 1000, or at least 2000, or at least 3000 or at least 3500, or at least 4000, or at least 5500; and its weight average molecular weight may be less than 15,000 or less than 12,000, or up to 8000 (g/mole). In this embodiment, the thermoplastic adhesive component may be free of plasticizers of a weight average molecular weight below 1000 g/mole, or below 2000 g/mole.

In another embodiment, or additional embodiment, the plasticizer may be hydrophilic. It may thereto be a solid (at 20° C.) compound that is water-dispersible; or it may be water-soluble, for example water-soluble, have a water-solubility of at least 30% or at least 40% or at least 50%, as defined by the method described herein below. It may then have any weight average molecular weight, but typically from at least 300 g/mole to 10,000 g/mole, or in one embodiment, from 1000 g/mole to 8000 g/mole.

Plasticizers include oils and waxes, provided of a weight average molecular weight of at least 1000; in one embodiment, it may however be that no oils or waxes are present; it may be that (the more hydrophilic) esters of oils and fats are used as plasticiser(s), including glycerol esters of fatty acids (e.g. derived from fat or oil), or such polymerised compounds, or for example PureSyn (PureSyn 3E20) esters.

Some exemplary plasticizers include: polyethylene glycols (PEG's), polypropylene glycol (PPG's), alcohol ethoxylates, and/or any derivatives thereof.

In one embodiment, the thermoplastic adhesive component comprises a polyethylene glycol, polypropylene glycol, alcohol ethoxylates, and/or any derivatives thereof of a MW of below 1000, for example, PEG 400 used (which is (at 20° C.) a liquid, with MW=400 (on average)).

In another embodiment, or in addition, the thermoplastic adhesive component may comprise a polyethylene glycol, polypropylene glycol, alcohol ethoxylates, and/or any derivatives thereof of a MW of at least 1000, for example PEG 10000 may be used (which is (at 20° C.) a solid, with MW=10,000 (and MW is between 8500-11500)).

In some embodiment, a long chain ethoxylated alcohol such as Unitox Ethoxylate 420 or 450, or a glycerin, glycerol, sorbitol, or ester compound, including citric acid esters may be useful as plasticizer.

It may comprise a plasticizer that is solid at 20° C., but liquid at higher temperatures, e.g. at process temperatures, e.g. above 60° C. or above 100° C. For example, a benzoate derivative may be used, such as 4-cyclohexane dimethanol dibenzoate, for example Benzoflex 352.

The plasticizer may alternatively, or in addition, comprise a polyalphaolefins (hydrogenated) synthetic hydrocarbon plasticizer, e.g. provided of average Molecular weight of 1000 or more (such as Durasyn 180; being of average MW=2000).

Also useful plasticizers include branched polyalkanes or branched polyalkenes, such as branched butane hydrocarbon polymers, e.g., of Mw of 1000 or more, including for example Indopol H-6000 of weight average MW=7560, and alternatively Indopol H-15.

The glass transition temperature of the plasticizer may be above room temperature (20° C.), or for example 40° C. or more, or 60° C. or more, as can be measured by ASTM E1356-03.

A typical level of the plasticizer is from 0.5 to 50%, or 1% to 45% or 5% to 45%, or 10% to 40% by weight of the thermoplastic adhesive component.

In one embodiment, a tackifying agent may be included in the thermoplastic adhesive component, as known in the art, in particular in thermoplastic adhesive component that include styrene-based polymers, e.g. styrenic block (co)polymer(s). In one embodiment, the tackifying agent has a weight average molecular weight of at least 1000, or at least 2000 or at least 3000 or at least 4000. It may be a material that is solid at 20° C. In one embodiment, the thermoplastic adhesive component is substantially free of tackifying agents of a weight average molecular weight of below 1000.

Alternatively, or in addition, the tackifying agent may be hydrophilic. It may thereto be a solid (at 20° C.) compound that is water-dispersible; or it may be water-soluble, for example water-soluble, have a water-solubility of at least 30% or at least 40% or at least 50%, as defined by the method described herein below.

Suitable tackifying agents include: rosin, rosin derivatives, including rosin esters. Typical concentrations (levels) of the tackifying agent in the thermoplastic adhesive component herein are in the range of from 7% or from 10% or from 20% or from 30%, to 70% or to 60% or to 50% by weight of the component. It is also envisaged herein that the thermoplastic adhesive component comprises a thermoplastic polymer as described herein above and a tackifying agent, as described herein, and only optionally a plasticizer, as described herein.

Furthermore, other additives may be added, such as stabilizers, chain terminators, UV protecting agents, antioxidants, and bacteriostats to help prevent thermal, oxidative, and biochemical degradation. Thermoplastic adhesive components including SBC may include end-block reinforcers, e.g. if the end use is for higher temperature applications. Examples of end-block reinforces include aromatic C9 and coumarone-indene compounds. The thermoplastic adhesive component herein may also include inorganic particulate material, including pigments, e.g. zinc oxide, titanium dioxide, clay (hydrated aluminum silicate), silica (silicon dioxide, may be hydrated), talc (magnesium silicate) and whitening agents (calcium carbonate).

In one embodiment herein, it may be that the thermoplastic adhesive component includes 30% to 70%, up to 60%, by weight of one or more thermoplastic polymers, such as SBS or EVA, and 10% or 20% to 50% by weight of a tackifying agent, as described above, and 5% to 30%, 10-40%, or 20-30% by weight of plasticizer, as described above.

The thermoplastic adhesive component may be combined with, or applied to, the surface-modified water-absorbing polymeric particles such that it is present as a coating or partial coating. The thermoplastic adhesive component may be such that it can be fiberized, and it may be that it is present in the absorbent layer in the forms of fibres, i.e. the thermoplastic adhesive component is fiberized or fibrous. It may be that it forms a fibrous matrix for the surface-modified water-absorbing polymeric particles.

The thermoplastic adhesive fibres may have an average thickness of 1-50 micrometer and an average length of 5 mm to 50 cm.

Absorbent Articles and Absorbent Layer(s) Thereof

The absorbent article herein includes at least one absorbent layer including the thermoplastic adhesive component and the surface modified water-absorbing polymeric particles, as described herein.

The absorbent layer may be the absorbent core, or a layer thereof, of an absorbent article. When it is part of an absorbent core, it may for example be the storage layer, designed to store bodily fluids; or an acquisition layer, designed to receive and distribute bodily fluids, and to pass the fluids to another layer(s), such as a storage layer below. The absorbent article may also include an absorbent core with a multitude (e.g. more than 1) of the absorbent layers, for example an acquisition layer and storage layer, each including the surface modified water-absorbing polymeric particles and thermoplastic adhesive components, described herein.

The absorbent layer has a Z-direction thickness, and a width (X-direction) and length (Y-direction). The absorbent layer has typically a surface area (X-Y plane) of at least 4 cm2, or at least 10 cm2 or at least 20 cm2. In one embodiment, the absorbent layer includes at least 1 gram of the surface modified water-absorbing polymeric particles, or at least 3 grams or at least 5 grams. The absorbent layer may have for example a volume of at least 1 cm3, or at least 5 cm3 or at least 10 cm3 (when laid out flat, under normal atmospheric pressure, conditioned for 24 hrs at 20° C., 50% relative humidity).

In one embodiment, the absorbent layer is free of absorbent cellulosic fibres. In one embodiment, the absorbent layer includes an absorbent portion with the thermoplastic adhesive component and the surface-modified water-absorbing polymeric particles, enclosed by one or more sheet materials, such as a nonwoven sheet.

Then, the thermoplastic adhesive component and the surface-modified water-absorbing material may form together at least 85%, or at least 90% or even at least 95% by weight of the absorbent portion of the absorbent layer (e.g. absorbent layer minus enclosing sheet materials).

In one embodiment, the absorbent layer includes the surface modified absorbent polymeric particles and the thermoplastic adhesive component in a weight ratio as described above.

The absorbent layer can be made by any method involving combining the thermoplastic adhesive component and the surface-modified water-absorbing particles. Typically, the thermoplastic adhesive component is present in the form of fibres and the process to make the absorbent layer involved fiberizing the thermoplastic adhesive component.

The thermoplastic adhesive component may be applied by spraying it in liquid form onto the surface-modified water-absorbing polymeric particles, for example by use of spray nozzle(s).

The absorbent layer typically herein includes also a substrate sheet material, such as a core wrap or core cover. The substrate sheet material herein may be any material, e.g. layer or sheet, capable to hold, or support or contain water-absorbing polymers. Typically, it is a web or sheet material, such as a foam, film, woven web and/or nonwoven web, as known in the art. The substrate may include spunbond, meltblown and/or carded nonwovens. A material may be a so-called SMS material or SMMS material, including a spunbond layer, one or two, respectively, melt-blown layers and a further spunbond layer. It may be permanently hydrophilic nonwovens, and/or nonwovens with hydrophilic coatings. The substrate material may enclose the absorbent component herein. The substrate material may include a top layer and the bottom layer, which may be made of a unitary material, in which case this material is folded to form a top and bottom layer, or it may be made of two or more separate sheets or webs. The substrate is typically made of one or more sheets or layers that are bonded together to enclose the water-absorbing component therein, e.g. by adhesive bonding and/or heat bonding. Some nonwoven materials are provided from synthetic fibres, such as polyethylene, PET and may be polypropylene. As the polymers used for nonwoven production may inherently be hydrophobic, they may be coated with hydrophilic coatings, e.g., coated with nanoparticles, as known in the art. Nonwoven materials and absorbent structures using such materials are described in, for example, co-pending applications US 2004/0162536, EP1403419-A, WO2002/0192366, EP1470281-A and EP1470282-A.

Absorbent layers for use in absorbent articles herein may include a substrate material sheet and thereon one or more layers of the surface-modified water-absorbent polymeric particles and the thermoplastic adhesive component (together the "absorbent component" referred to below). The surface-modified water-absorbing polymeric particles and thermoplastic adhesive component may each be present as separate layer or layers, or they may be present, mixed together, as one or more mixed layers.

Thereby, the thermoplastic adhesive component can provide a matrix, e.g. cavities or network, for the water-absorbing polymeric particles e.g. to hold them in the cavities or network.

The absorbent component or the surface-modified absorbent polymeric particles of an absorbent layer may be discontinuous and/or profiled in Z, X or Y direction.

An absorbent layer or layers can for example be made as follows:
a) providing one or more substrate sheet materials (together forming the substrate, as referred to herein), e.g. that can serve as a wrapping or partial wrapping material;
b) providing surface-modified water-absorbing polymeric particles;
c) providing a thermoplastic adhesive component, as described herein;
and then forming a water-absorbent layer by either:
d) depositing the thermoplastic adhesive component on the substrate sheet material and then the surface modified water-absorbing polymeric particles onto the thermoplastic adhesive component; and/or
e) depositing the surface-modified water-absorbent polymeric particles on the substrate sheet material and then the thermoplastic adhesive component onto the surface-modified water-absorbent polymeric particles; and/or
f) mixing the thermoplastic adhesive component and water-absorbent polymeric particles and then depositing the mixture on the substrate sheet material; and then:
g) enclosing the resulting component with the substrate sheet material(s) and typically sealing the substrate sheet material; or
h) repeating steps a) to f) to obtain two or more absorbent components which are then combined to form the final absorbent component, and then applying step g) above, to obtain the absorbent layer, typically by ensuring the substrate sheet materials of each component form one of the outer surfaces of the absorbent layer.

Optionally, the surface-modified water-absorbent polymeric particles and/or the thermoplastic adhesive component and/or the mixture thereof may be applied in a pattern with varying dimensions, e.g. thickness, width or length, and/or in a pattern, so that the absorbent layer includes at least one zone which is substantially free of one or more of these compounds and the pattern including at least one or at least two zones including the surface-modified water-absorbing polymeric particles (and may be such that openings are formed between the separate zones with surface-modified water-absorbing polymeric particles).

Some (disposable) absorbent articles including the absorbent layer include sanitary napkins, panty liners, adult incontinence products (diapers, briefs) and infant (baby and toddler) diapers, including training pants. The articles may serve to absorb urine, e.g., adult incontinence products and infant diapers.

The absorbent articles herein have typically a topsheet and a backsheet, which each have a front region, back region and crotch region, positioned therein between. The absorbent component or core, or structure, as described herein is typically positioned in between the topsheet and backsheet. Some backsheets are vapor pervious but liquid impervious. Some topsheet materials may be at least partially hydrophilic; and may also be so-called apertured topsheets. It may be that the topsheet includes a skin care composition, e.g. a lotion composition.

Because the water-absorbing material herein has a very high absorbency capacity, it is possible to use only low levels of this material in the absorbent articles herein. Some may be thin absorbent articles, such as adult and infant diapers, training pants, sanitary napkins including an absorbent structure of the present disclosure, the articles having an average caliper (thickness) in the crotch region of less than 1.0 cm, less than 0.7 cm, less than 0.5 cm, or even less than 0.3 cm (for this purpose alone, the crotch region being defined as the central zone of the product, when laid out flat and stretched, having a dimension of 20% of the length of the article and 50% of the width of the article).

Because the water-absorbing material herein has a very good permeability, there is no need to have large amounts of traditional structuring agents present, such as absorbent (cellulose) fibres, such as airfelt, and may thus be omitted or only used in very small quantities, as described above. This further helps to reduce the thickness of the absorbent structure, or absorbent articles herein.

Some articles according to the present disclosure achieve a relatively narrow crotch width, which increases the wearing comfort. One article according to the present disclosure achieves a crotch width of less than 100 mm, 90 mm, 80 mm, 70 mm, 60 mm or even less than 50 mm, as measured along a transversal line, which is positioned at equal distance to the front edge and the rear edge of the article, or at the point with the narrowest width. Hence, an absorbent layer herein may have a crotch width as measured along a transversal line which is positioned at equal distance to the front edge and the rear edge of the core which is of less than 100 mm, 90 mm, 80 mm, 70 mm, 60 mm or even less than 50 mm. It has been found that for most absorbent articles the liquid discharge occurs predominately in the front half.

A diaper herein may have a front waist band and a back waist band, whereby the front waist band and back waist band each have a first end portion and a second end portion and a middle portion located between the end portions, and whereby the end portions may include each a fastening system, to fasten the front waist band to the rear waist band or whereby the end portions may be connected to one another, and whereby the middle portion of the back waist band and/or the back region of the backsheet and/or the crotch region of the backsheet includes a landing member, wherein the landing member may include second engaging elements selected from loops, hooks, slots, slits, buttons, magnets. Examples include hooks, adhesive or cohesive second engaging elements. It may be that the engaging elements on the article, or diaper are provided with a means to ensure they are only engagable at certain moments, for example, they may be covered by a removable tab, which is removed when the engaging elements are to be engaged and may be re-closed when engagement is no longer needed, as described above.

Some diapers and training pants herein have one or more sets of leg elastics and/or barrier leg cuffs, as known in the art.

It may also be that diaper has a secondary topsheet, in contact with the skin and may be overlaying a primary topsheet, as for example described above, the secondary topsheet having an elongated slit opening, may be with elasticiation means along the length thereof, where through waste material can pass into a void space above the absorbent structure, and which ensures the waste material is isolated in this void space, away from the wearer's skin.

Examples and Methods Used Herein:

The following test methods used herein are described in co-pending application WO2006/083585, i.e. methods for: preparation of films of the elastic film-forming polymer; polymer molecular weights determination; water-swelling capacity of a polymer determination.

Water Solubility

Water solubility of the components herein is determined as follows: 100 mg starting amount (SA) of the component or compound is applied to a glass slide (2.5 cm×8 cm) of known weight, such that the material covers an area of 2.5 cm×5 cm on the glass slide. The slide is then placed flat in a beaker (having a diameter of 9 cm) containing 75 ml of deionized water at 20° C. The water (with the dissolved material or polymers) is not stirred. After 4 hours the glass slide is removed from the beaker and put in an oven at 60° C., 0% RH (relative humidity) for 2 hours, to remove the water. After drying it is weighted to determine the residual amount of material or polymers on the slide. A compound or component herein, e.g. the thermoplastic adhesive component of the present disclosure, is water-soluble if the residual amount (RA) thereof on the plate after drying is below 70% (solubility of at least 30%), and may be below 65% (solubility of at least 35%) etc., as described herein (of the 100 mg that have been applied to the glass slide): as follows:

$$[(SA-RA)]/SA \times 100\% = \text{water solubility (in \%)}$$

Absorbency/Adhesive Interaction Test

The following includes examples of the preparation of samples of surface-modified water-absorbing polymeric particles and a thermoplastic adhesive components, according to the invention and of samples of surface-modified water-absorbing polymeric particles and a thermoplastic adhesive component outside the scope of the invention; and the testing thereof in the absorbency/glue interaction test, described below, to evaluate the impact of the glue on the absorbency of the surface-modified water-absorbing polymeric particles.

Surface-modified water-absorbing polymeric particles were prepared as follows:

Surface-Treated (i.e. Coated) Water-Absorbent Polymeric Particles

Water-absorbent polymeric particles ASAP 510 Z (ex. BASF A; sold with a particle size range 150-850 μm) were coated with Permax 200 (Noveon, Brecksville, Ohio' polyurethane polymer, as described above), at an add-on level of 2.5% Permax, and a deagglomeration aid, as follows.

A Wurster coater (available at The Coating Place) was used for the coating step. The Wurster tube was 50 mm in diameter and 150 mm in length, the gap width (distance from base plate) was 15 mm, the Wurster apparatus was conical with a lower diameter of 150 mm expanding to an upper diameter of 300 mm, the carrier gas used was nitrogen having a temperature of 24° C., the gas speed was 3.1 m/s in the Wurster tube and 0.5 m/s in the surrounding annular space.

An aqueous water-absorbent polymer particles (ASAP 5 10Z) dispersion was made and atomized using a nitrogen-driven two-material nozzle, opening diameter 1.2 mm, (from Fa. Schlick (Germany) operated in bottom spray mode, opening diameter 1.2 mm, the nitrogen temperature being 25° C.).

The Permax 200 dispersion was sprayed as an 11% by weight aqueous dispersion. The inlet temperature and coating bed temperature was 170° C.

After spraying of the Permax dispersion was finished, 0.5% by weight (of the uncoated water-absorbent polymeric particles) of tricalcium phosphate dispersion was added, as deagglomeration aid, into the coater and fluidized with the coated particles for 5 minutes, to ensure it was present at the particles homogeneously. Then, the coated particles were annealed at 175 ° C. for 5 min in the coater. Then, the thus coated water-absorbent polymeric particles were sieved, to obtain the 150-500 μm fraction only, which was used in the testing herein.

Preparation of Adhesive Components for the Tests:

Into a 70 mm diameter aluminum tray (same tray used in absorbency/adhesive interaction test below; GRT0471-61), 5 gr of the adhesives component, comprising 70% by weight of for example Cycloflex (comprising a thermoplastic component) and a 30% by weight of the additional plasticizer (e.g. for example PEG, specified below), is added. (except for example D below, where the weight ratio was 80;20).

The tray is placed into a 165° C. vented oven for at least 5 minutes, until the adhesive component is melted/flowable. If necessary, a higher temperature is chosen to ensure the mixture melts/flows.

The tray is removed from the oven; the molten/flowable adhesive component is stirred with a wooden (disposable) stick to thoroughly mix the component.

This is repeated 5 times, to ensure a substantially homogeneous adhesive component. Then, the tray is placed into the oven again for 10 minutes, to achieve a uniform layer of the adhesive component in the bottom of the tray.

The tray is then removed and cooled to room temperature, obtain a 5 gr. Adhesive component sample ready for testing. (This procedure is repeated for each of the samples required in the tests.)

The following 5 gr. adhesive component samples were made via this procedure (in weight ratios):

Adhesive Component A:
70:30 Cycloflex 34-5653 (ex National Starch): Durasyn 180 (MW 2000; ex Innovene)

Adhesive Component B:
70:30 Cycloflex 34-5653 (ex National Starch): Indopol H15 (ex Innovene)

Adhesive Component C:
70:30 Cycloflex 34-5653 (ex National Starch): Indopol H-6000 (ex Innovene)

Adhesive Component D:
80:20 Cycloflex 34-5653 (ex National Starch): PEG 400 (ex Aldrich)

Adhesive Component E:
70:30 Cycloflex 34-5653 (ex National Starch): PEG 10,000 (ex Aldrich)

Adhesive Component F:
70:30 Cycloflex 34-5653 (ex National Starch): PureSyn $3^E20$ (ex Exxon Mobile)

Adhesive Component G:
70:30 Cycloflex 34-5653 (ex National Starch): Durasyn 164 (MW 443; ex Innovene) (outside the scope of the invention)

Adhesive Component H:
70:30 Cycloflex 34-5653 (ex National Starch): Britol 50T (ex Sonnebom) (outside scope of the invention)

Adhesive Component I
Fuller NW1151 (outside the scope of this invention)

Adhesive-Coated Water-Absorbent Polymeric Particle Samples A-I: Preparation, and Aging For each test sample to be used in the test below, a tray with one of the adhesive component A-H is used, as prepared above; or a tray with adhesive I, the latter being prepared as follows:
a tray with adhesive I, as described above, is placed into a preheated 165° C. vented oven as above, but for about 1 hour, so that the adhesive component is soft enough to flow. The tray is then removed from the oven and gently tilted from side to side to ensure an even coating of flowable adhesive I across the bottom surface of the tray.

Each of the trays is covered and cooled (to 20° C.) and then weighed ($W_{tray}$)

Per Tray:

The water-absorbent polymeric particle sample is shaken, to ensure uniform particle distribution throughout the sample. With a spatula, 0.50 g of the test coated water-absorbent polymeric particles is weighed ($W_{dryAGM}$), and then sprinkled evenly over the entire surface of the adhesive component in the tray, ensuring uniform coverage. Then, the tray is weighed again ($W_{Tray+dryAGM}$).

The sample trays thus prepared will be either tested immediately (to get a test value for the fresh sample) or "aged" (e.g. stored 16 hrs and/or 1 week at 60° C. in vented oven).

Absorption/Adhesive Interaction Test:

This test determines the absorption within a set time (e.g. 30 seconds) for a sample, including surface-modified water-absorbing polymeric particles and a thermoplastic adhesive material, as prepared above, after aging (i.e. for 1 week at 60° C.). Per sample, 3 trays should be prepared, to obtain 3 measurements per aged sample type (1 week at 60° C.). The test may also be repeated with fresh samples of the samples above, obtained immediately after mixing. Then also 3 trays should be prepared and tested immediately.

These tests thereby serve to determine for such a sample (a mixture of water-absorbing polymeric polymers and a thermoplastic adhesive component) the impact of the presence of the thermoplastic adhesive component on the absorption, and/or the impact thereof over time.

The tray and a cup with a screen at the bottom are weighed to (obtain a combined weight of said tray and cup $W_{combined}$). The cup is of Plexiglas and has a screen on the bottom. The cup has the following dimensions: 60 mm ID, 70 mm OD, 60 mm height and screen is a 100 mesh. The cup is then placed onto 10 plies of Ahlstrom Grade 989 (4"×4") filter paper. With a dispenser, exactly 20 mL of 0.9% saline solution dyed with 20 ppm Toluidine Blue, is measured and added into the tray, within 3 seconds. Then, the water-swellable polymeric particles/adhesive component mixture is allowed to absorb this saline solution for exactly 30 seconds.

After exactly 30 seconds, the solution is poured from the tray into the cup (removing the excess liquid not absorb by the AGM but preventing the AGM from passing through the screen in the bottom of the cup). The tray is gently tapped against the top of the cup to remove any residual liquid. After exactly 30 seconds of draining, the tray and cup are weighed again ($W_{combined+saline\ absorbed}$).

The weight of the absorbed saline can then be calculated ($W_{saline\ absorbed}$)=$W_{combine+saline\ absorbed}$−$W_{combine}$.

Then the absorption in g/g can be calculated:

$$(W_{saline\ absorbed})(g)/W_{dryAGM}(g) = \text{Saline absorption (g/g)}.$$

This is repeated twice, to obtain 3 absorbed fluid values, and this is then averaged, to obtain the average saline absorption (g/g) of a certain sample ($SA_{aged\ average}$).

This test is repeated for each of the other aged samples (1 week at 60° C.), in each case 3 times, to obtain average saline absorption values (g/g) per sample ($SA_{aged\ average}$).

The test is also done for a sample of the coated water-absorbent polymeric particles (herein referred to as AGM) prepared as set out above, but not comprising any adhesive component (or any additive). This is per AGM sample done 3 times, to obtain an average over 3 samples (e.g. aged samples), $SA_{aged\ AGM\ average}$. Then, the average amount of saline absorbed by an aged sample (A to F, or G or H), aged for 1 week at 60° C., $SA_{aged\ sample\ average}$ (as described above) can be compared with the average amount of saline absorbed by an aged sample of the coated water-swellable absorbent particles without thermoplastic adhesive component (said aged sample being aged for 1 week at 60° C., in the manner described above), $SA_{aged\ AGM\ average}$. (The same comparison may be done for the fresh samples). Such differences in the amount of saline absorbed by the aged AGM sample and of any of the aged samples A-J can be calculated and reported as (in %):

$$(SA_{aged\ AGM\ average} - SA_{aged\ sample\ average}) / (SA_{aged\ AGM1\ sample\ average}) \times 100\ (\%)$$

The test may also be done for all of the fresh samples (3 times per sample) and the $SA_{fresh\ average}$ or $SA_{freash\ AGM\ average}$ may be calculated in the same manner; and in the same manner the $SA_{fresh\ average}$ of a sample A-I may be compared with the $SA_{freash\ AGM\ average}$ or with $SA_{aged\ average}$ of a specific sample.

In one embodiment herein, ($SA_{aged\ AGM\ average} - SA_{aged\ sample\ average}) / (SA_{aged\ AGM1\ sample\ average}) \times 100\ (\%)$ is less than 20%, more preferably <10%, most preferable <5%.

| Samples | Average Saline absorption (g/g) after 1 Week Aging, 60 C. | St. Dev. |
| --- | --- | --- |
| (coated) AGM (no adhesive) | 3.52 | 0.18 |
| Sample I | 2.34 | 0.08 |
| Sample H | 2.22 | 0.13 |
| Sample G | 1.62 | 0.07 |
| Sample A | 3.19 | 0.04 |
| Sample B | 3.83 | 0.47 |
| Sample C | 3.55 | 0.22 |
| Sample D | 4.28 | 0.09 |
| Sample E | 3.76 | 0.04 |
| Sample F | 3.24 | 0.19 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising an absorbent layer comprising:
   a) a thermoplastic adhesive component having a viscosity of from 800 to 4000 mPa·s, at 175° C. (as defined herein) and comprising:
      (i) a thermoplastic polymer having a weight average molecular weight of at least 8000 g/mole; and
      (ii) a plasticizer having a weight average molecular weight of at least 3000 g/mole; and
      wherein the thermoplastic adhesive component is substantially free of plasticizers having a weight average molecular weight below 3000 g/mole, wherein the thermoplastic adhesive component is free of waxes;
   b) surface-modified water-absorbing polymeric particles comprising: a surface modification agent including a coating agent, forming a coating or partial coating on the particles; and
   c) wherein the thermoplastic adhesive component contacts the surface-modified water-absorbing polymeric particles, wherein the thermoplastic adhesive material forms a coating on and a fibrous matrix for the surface-modified water-absorbing polymeric particles.

2. The absorbent article of claim 1, whereby the thermoplastic adhesive material is fiberized.

3. The absorbent article of claim 1, wherein the thermoplastic adhesive component is substantially free of tackifying agents and plasticizers having a weight average molecular weight below 3000 g/mole.

4. The absorbent article of claim 1, wherein the thermoplastic adhesive component comprises a thermoplastic polymer selected from the group consisting of: a polyolefin, an EVA, a SBC, and mixtures thereof.

5. The absorbent article of claim 1, wherein the plasticizer is selected from the group consisting of: esters of oils; esters of fats; polyethylene glycols and derivatives thereof; polypropylene glycols and derivatives thereof; and ethoxylated alcohols and any derivatives thereof.

6. The absorbent article of claim 1, wherein the thermoplastic adhesive component comprises a rosin ester tackifying agent.

7. The absorbent article of claim 1, wherein the surface-modifying agent is a coating agent and comprises a film-forming and a phase-separating elastic polymer including a polyurethane.

8. The absorbent article of claim 1, wherein the surface-modified water-absorbing polymeric particles have a mean particle size between 200 and 800 microns and wherein less than 10% by weight of the particles have a particle size of below 150 microns.

9. The absorbent article of claim 1, wherein the absorbent layer comprises the surface-modified water-absorbing polymeric particles and the thermoplastic adhesive component at a weight ratio of from 10:1 to 100:1, and wherein the absorbent layer comprises less than 1% by weight of absorbent cellulosic fibres.

10. An absorbent article comprising an absorbent layer comprising:
   a) a thermoplastic adhesive component having a viscosity of from about 800 to about 4000 mPa·s, at 175° C. (as defined herein) and comprising:
      (i) a thermoplastic polymer having a weight average molecular weight of at least 8000 g/mole;
      (ii) a plasticizer being water-soluble and having a water-solubility of at least 30%, wherein the plasticizer has a weight average molecular weight of at least 3000 g/mole; and
      the thermoplastic adhesive component is substantially free of tackifying agents and plasticizers having a weight average molecular weight below 3000 g/mole, wherein the thermoplastic adhesive component is free of waxes;
   b) surface modified water-absorbing polymeric particles comprising a surface modification agent including a coating agent forming a coating on the particles; and
   c) wherein the thermoplastic adhesive component contacts the surface-modified water-absorbing polymeric particles, wherein the thermoplastic adhesive material forms a coating on and a fibrous matrix for the surface-modified water-absorbing polymeric particles.

11. The absorbent article of claim 10, wherein the thermoplastic adhesive material is fiberized.

12. The absorbent article of claim 10, wherein the thermoplastic adhesive component comprises a thermoplastic polymer selected from the group consisting of: a polyolefin, an EVA, a SBC, and mixtures thereof.

13. The absorbent article of claim 10, wherein the plasticizer is selected from the group consisting of: esters of oils, esters of fats, polyethylene glycols and derivatives thereof, polypropylene glycols and derivatives thereof, and ethoxylated alcohols and any derivatives thereof.

14. The absorbent article of claim 10, wherein the thermoplastic adhesive component comprises a rosin ester tackifying agent.

15. The absorbent article of claim 10, wherein the surface-modifying agent is a coating agent and comprises a film-forming and phase-separating elastic polymer including a polyurethane.

16. The absorbent article of claim 10, wherein the surface-modified water-absorbing polymeric particles have a mean particle size between 200 and 800 microns and less than 10% by weight of the particles have a particle size of below 150 microns.

17. The absorbent article of claim 10, wherein the absorbent layer comprises the surface-modified water-absorbing polymeric particles and the thermoplastic adhesive component at a weight ratio of from 10:1 to 100:1, and wherein the absorbent layer comprises less than 1% by weight of absorbent cellulosic fibres.

18. An absorbent layer comprising:
   surface-modified water-absorbing polymeric particles comprising:
a surface-modifying polymeric coating agent of a thermoplastic adhesive component to form a fibrous matrix for the particles, the thermoplastic adhesive component having a viscosity of from 800 to 4000 mPa·s, at 175° C. (as defined herein) and comprising a thermoplastic polymer with a weight average molecular weight of at least 8000 g/mole, and a plasticizer of a weight average molecular weight of at least 3000 g/mole, and being substantially free of tackifying agents and plasticizers having a weight average molecular weight below 3000 g/mole, wherein the thermoplastic adhesive component is free of waxes.

\* \* \* \* \*